(12) United States Patent  (10) Patent No.: US 6,745,773 B1
Gobel  (45) Date of Patent: Jun. 8, 2004

(54) TRACHEAL TUBE

(75) Inventor: Fred G. Gobel, Regensburg (DE)

(73) Assignee: Dr. Fred Goebel Patentverwaltung GmbH, Heidelberg (DE)

( * ) Notice: Subject to any disclaimer, the term of this patent is extended or adjusted under 35 U.S.C. 154(b) by 0 days.

(21) Appl. No.: 09/254,395

(22) PCT Filed: Sep. 8, 1997

(86) PCT No.: PCT/EP97/04891

§ 371 (c)(1),
(2), (4) Date: Jun. 3, 1999

(87) PCT Pub. No.: WO98/10819

PCT Pub. Date: Mar. 19, 1998

(30) Foreign Application Priority Data

Sep. 10, 1996 (DE) .......................................... 196 36 654
Sep. 23, 1996 (DE) .......................................... 196 38 935

(51) Int. Cl.⁷ ............................................. A61M 16/00

(52) U.S. Cl. ........................... 128/207.15; 128/207.14; 128/204.18; 604/99.01; 604/101.01

(58) Field of Search .......... 128/200.24, 207.14–207.18; 606/191–200; 600/201, 204, 207, 210; 604/96.01–109

(56) References Cited

U.S. PATENT DOCUMENTS

| 3,640,282 A | 2/1972 | Kamen et al. |
| 3,669,098 A | 6/1972 | Takahashi |
| 3,766,924 A | 10/1973 | Pidgeon |
| 3,848,605 A | 11/1974 | Harautuneian et al. |
| 3,901,246 A | 8/1975 | Wallace |
| 3,931,822 A | 1/1976 | Marici |

(List continued on next page.)

FOREIGN PATENT DOCUMENTS

| DE | 24 00 569 | 7/1975 |
| DE | 24 12 553 | 9/1975 |
| DE | 30 18 608 | 1/1981 |
| DE | 30 36 192 | 5/1982 |
| DE | 32 09 413 | 9/1983 |
| DE | 34 35 849 | 4/1986 |
| DE | 35 42 260 | 6/1986 |
| DE | 87 11 592.1 | 10/1987 |
| DE | 39 18 956 | 12/1989 |
| DE | 40 12 296 | 10/1991 |
| DE | 41 32 687 | 4/1993 |
| DE | 23 41 833 | 2/1995 |
| DE | 295 11 468 | 11/1995 |
| DE | 195 47 538 | 6/1997 |
| DE | 196 38 935 | 3/1998 |
| DE | 196 54 910 | 3/1998 |
| EP | 0 277 797 | 8/1988 |
| EP | 0 596 517 | 5/1994 |
| EP | 0 697 205 | 2/1996 |
| FR | 1 561 588 | 3/1969 |
| GB | 1 060 629 | 3/1967 |
| WO | 98/10819 | 3/1998 |

OTHER PUBLICATIONS

Pschyrembel Klinisches Worterbuch, 1990, p. 1693, p. 439–440.

Primary Examiner—Glenn K. Dawson
(74) Attorney, Agent, or Firm—Bryan Cave LLP

(57) ABSTRACT

A tracheal tube by which the trachea is closed watertight by a fixation cuff blocking the trachea below the glottis, through which a ventilation cannula passes, and, situated cranially to it, above the cuff, a tampon-bladder made of flexible material expansible through the influx of fluid, which when filled differs in shape from the shape of the cuff, would represent an improvement by means of which a patient could be intubated in the gentlest way over a long period with minimal risk of infection. In the invention this is accomplished by situating the tampon-bladder immediately against the cuff and constructing it of foil-like material and so designing it that when fully distended in size it fills the subglottal space.

21 Claims, 6 Drawing Sheets

U.S. PATENT DOCUMENTS

Figure 1:
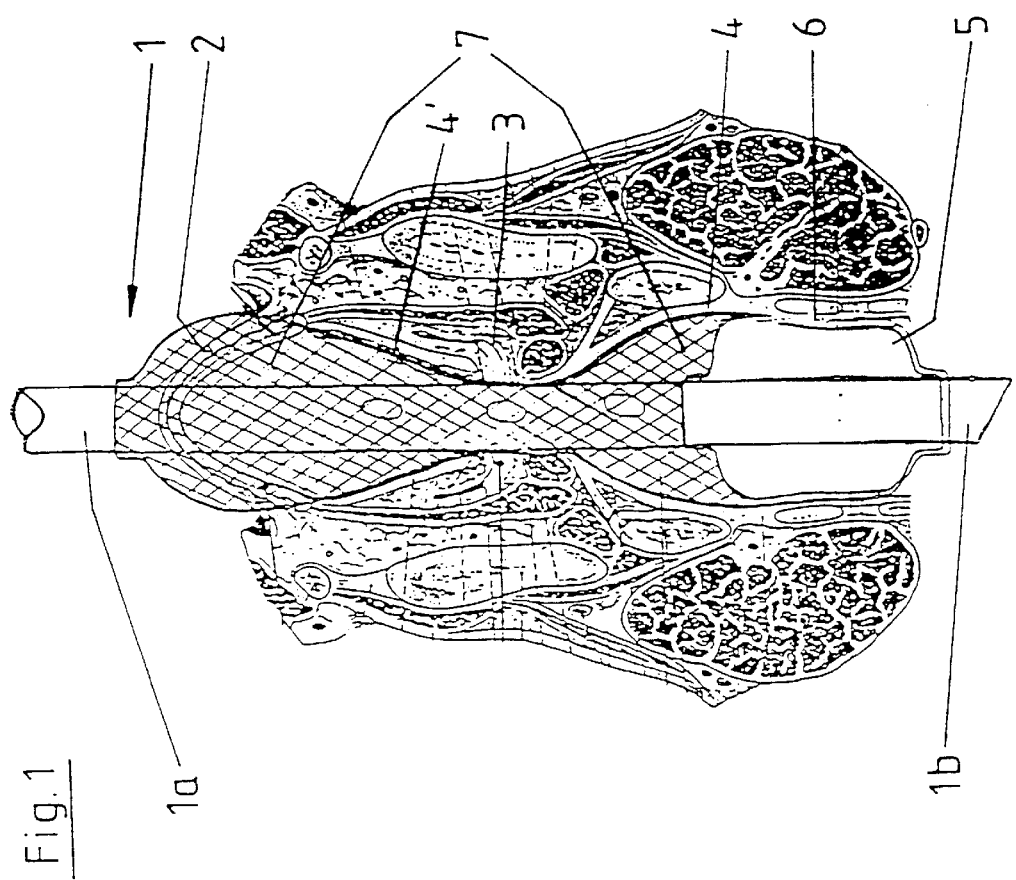

| | | | |
|---|---|---|---|
| 4,020,849 A | | 5/1977 | Jackson |
| 4,022,217 A | | 5/1977 | Rowean |
| 4,090,518 A | | 5/1978 | Elam |
| 4,091,816 A | | 5/1978 | Elam |
| 4,156,428 A | | 5/1979 | Henkin |
| 4,182,344 A | * | 1/1980 | Benson .................. 128/207.15 |
| 4,230,108 A | | 10/1980 | Young |
| 4,235,239 A | * | 11/1980 | Elam ..................... 128/207.15 |
| 4,387,711 A | | 6/1983 | Merry |
| 4,423,725 A | | 1/1984 | Baran et al. |
| 4,445,892 A | | 5/1984 | Hussein et al. |
| 4,449,523 A | | 5/1984 | Szachowicz et al. |
| 4,583,917 A | | 4/1986 | Shah |
| 4,700,700 A | | 10/1987 | Eliachar |
| 4,762,125 A | | 8/1988 | Leiman et al. |
| 4,791,923 A | | 12/1988 | Shapiro |
| 4,917,107 A | * | 4/1990 | Bell et al. ............... 128/207.15 |
| 5,033,466 A | | 7/1991 | Weymuller, Jr. |
| 5,040,531 A | | 8/1991 | Coleman et al. |
| 5,295,489 A | * | 3/1994 | Bell et al. ............... 128/207.15 |
| 5,318,021 A | * | 6/1994 | Alessi ................... 128/207.15 |
| 5,505,698 A | | 4/1996 | Booth et al. |
| 5,638,813 A | | 6/1997 | Augustine |

\* cited by examiner

TRACHEAL TUBE

DESCRIPTION

The invention concerned is a tracheal tube which closes the trachea against the flow of fluids by blocking it below the glottis with a fitted cuff through which a respiratory cannula passes, beside which cranially, above the cuff, is situated an inflatable tampon-bladder of flexible material which in its filled state takes a shape different from that of the cuff.

In one of the tracheal tubes of this kind described in U.S. Pat. No. 4,235,239 the cuff in its inflated state is approximately ball-shaped and constitutes a mooring fitted to the glottis. The cuff is designed to leave the subglottal space free. Situated above the cuff a second cuff is provided, which when inflated is approximately disc-shaped and when compressed fits water-tight above the glottis near the pharyngeal cavity. With this tracheal tube the glottis is compressed between the two cuffs, so that on prolonged intubation dangerous bruising and necrosis (tissue damage due to death of parts of the membrane) may result. There is in addition the risk of luxation (sliding out) of the tube.

In U.S. Pat. No. 5,033,466 a tracheal tube is presented in which a strongly inflated cuff is fitted to the respiratory passages under pressure to create a watertight closure. Situated above the cuff a second cuff filled with foam is provided at the narrowest diameter of the glottis, so that the harder respiratory cannula does not strike against and damage it.

With the use of a single cuff the low perfusion pressure on the vascular bed of the subglottal mucosa necessitates edging forward of the cuff of the tube over the cricoid cartilage into at least the region of the upper trachea. This results on intubation in a so-called subglottal space extending from the edge of the upper cuff to the vocal cords. During intubation pharyngeal secretion heavily contaminated with bacteria can leak unhindered into the subglottal space and incubate there, accessible to treatment only with difficulty.

The subglottal secretion endangers the artificially ventilated patient in two respects.

Because of inadequate sealing at the time of placing of the cuff, in the course of ventilation secretion manages continuously to pass the cuff barrier and on into the distal tracheobronchial system, and so is responsible for the development of the majority of all the pneumoniae (lung inflammations) associated with assisted respiration.

Furthermore stasis (damming up) of the subglottal secretion readily leads after a few days to inflammatory changes in the local mucous membrane. The chronic inflammatory process can go on to substantial consequent complications, such as e.g. the development of subglottal stenoses.

In U.S. Pat. No. 4,091,816 a tracheal tube with two fluid-associated cuffs is presented. The lower cuff is bullet-shaped, inelastic and for mooring is fitted to the glottis from below. The cuffs are separated from each other by a groove so that the glottis can interpose between the two cuffs. The upper cuff lies above the glottis and can expand into the pharyngeal cavity. Use of this tube carries the danger that the glottis will be damaged by compression. The extension of the upper cuff into the pharyngeal cavity can lead to autonomic stimulation, such as e.g. vagal reflexes, and thereby prepares the way for difficulties during the protracted phase of rehabilitation in a respirator.

In U.S. Pat. No. 4,449,523 a tracheal tube is proposed in which a first cuff is inflated watertight in the respiratory passages. Separate from the cuff is a second cuff for sealing the aperture in its neck through which the respiratory cannula passes. Between the cuffs airholes are provided inside the cannula. This avoids the risk that highly contaminated secretion might be inhaled through the holes.

In EP 0 277 797 A2 an operation tube for laser operations is described. Two identically designed cuffs are placed on a respiratory cannula. Both cuffs are blocked off for the duration of the operation so that they give a watertight fit to the respiratory tract under pressure. The upper cuff is intended as a buffer against possible injury by a laser instrument. This operation tube is intended only for short-term intubation during operations. In long-term intubation there might be the risk that on account of the deliberately minimalized surface of the laser tube and the deleterious build-up of pressure on the epithelium lesions of the tracheal epithelium would quickly develop.

In DE 295 11 468 U1 and G 87 115 92.1 tracheal tubes are described having two identically designed cuffs situated separately from each other.

It is the problem of the present invention to improve a tracheal tube of the kind mentioned at the beginning to the extent that a patient can be intubated without harm over a long period with only slight risk of infection.

This object is attained according to the invention by a tracheal tube with the features of Claim 1.

By the direct union of the tampon-bladder with the distal cuff the subglottal reservoir of pathogens is practically eliminated and a narrow gap between the tracheal mucosa and the inserted item, that is, the tampon-bladder, is reduced. The direct placing of the tampon-bladder on the cuff also results in an effectually continuous passageway in this region, since the reservoir of pathogens is reduced to just the narrow gap. In principle no pathogenic reservoir results, but only a thin film of secretion.

Pharyngeal secretion is forced back into the supraglottal region and penetration into the subglottal region substantially prevented. The infective path for the microbes of the pharyngeal secretion is lengthened maximally by the inserted item and with the tampon-bladder unfolded extends from the glottis to the lower margin of the cuff. Pathogens consequently require longer for passage of the infective pathway, and in the region of the narrow gap between the device and the mucosa they can be neutralized by the defence mechanisms of the epithelium itself and penetration into the distal respiratory passages impeded. Hence the solution provided by the invention makes it possible for the first time to use the body's own defence mechanisms for the avoidance of infections.

Since on unfolding the tampon-bladder no infectively sufficient subglottal volume of secretion remains, the risk of chronic subglottal stenosis due to inflammation can be excluded.

Since the tampon-bladder serves exclusively to fill the subglottal space, it can be applied so as to fulfil its purpose with epithelium-sparing minimal pressure. Pressure-associated necroses in the region of the subglottal mucosa can thus be avoided.

Advantageous characteristics and modes of employment of the invention are stated in the accompanying Claims.

Figure 2:
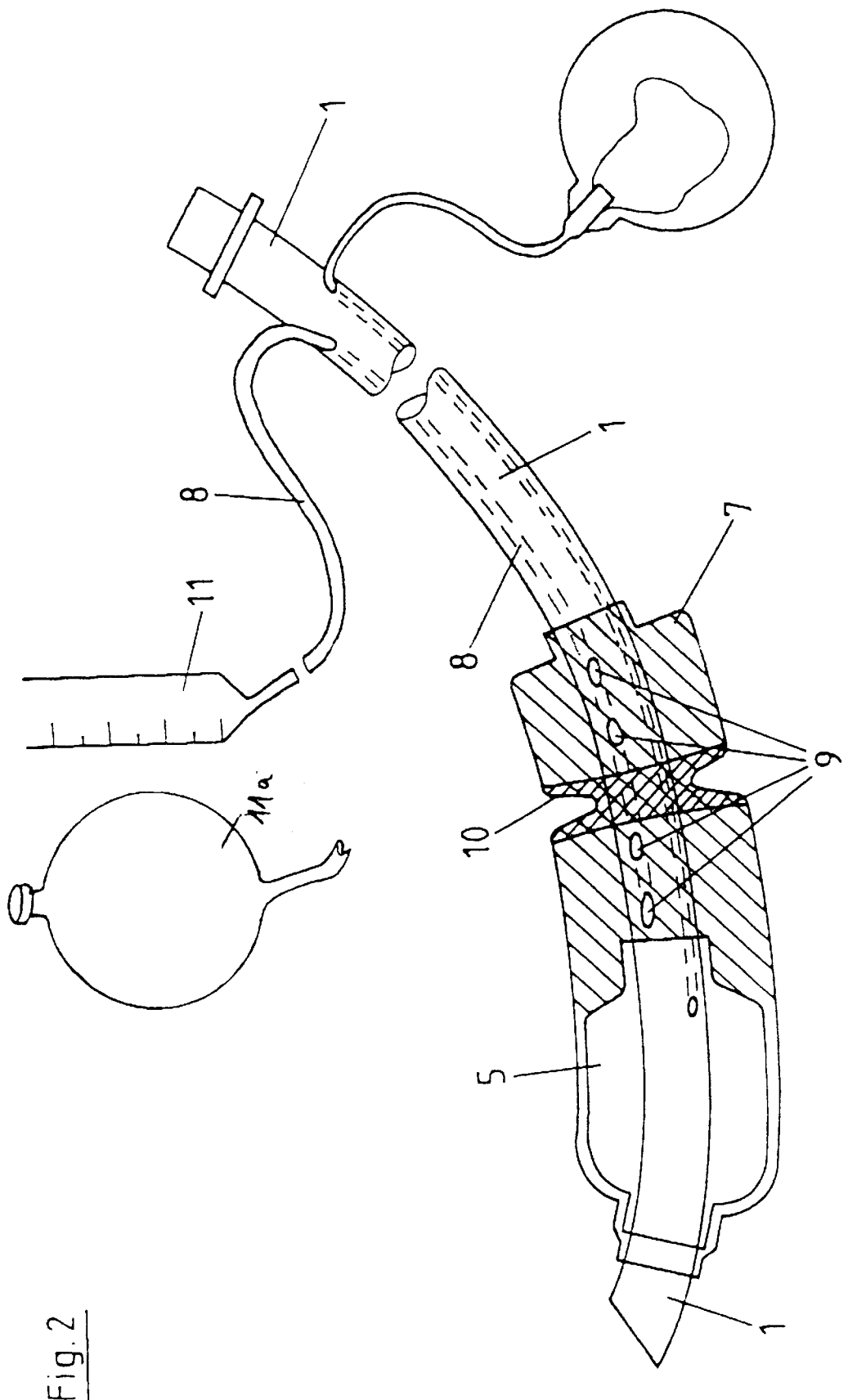
Figure 2A:
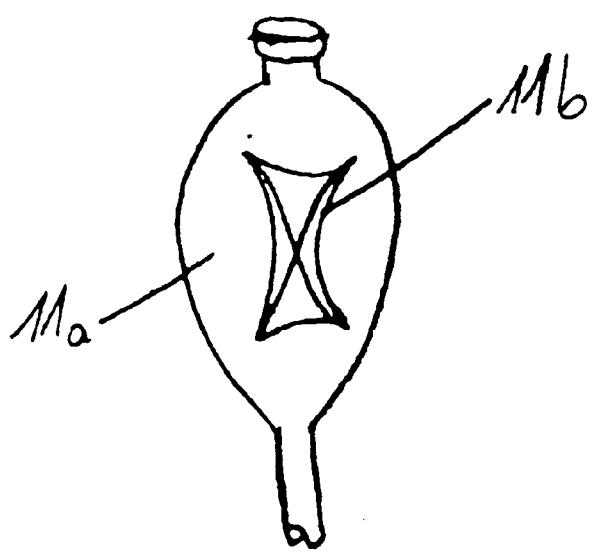
Figure 2B:
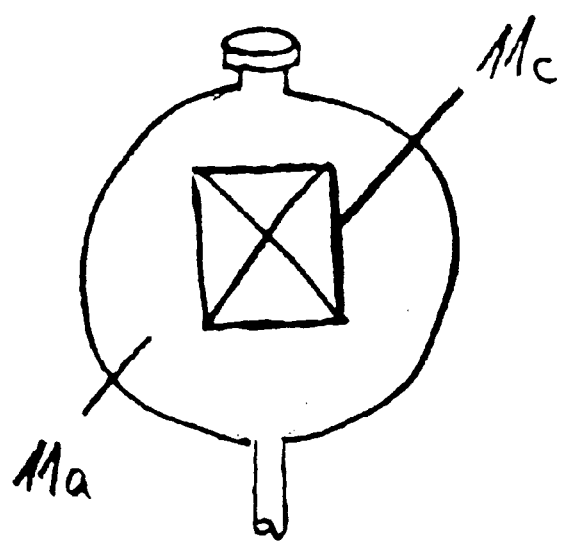
Figure 3:
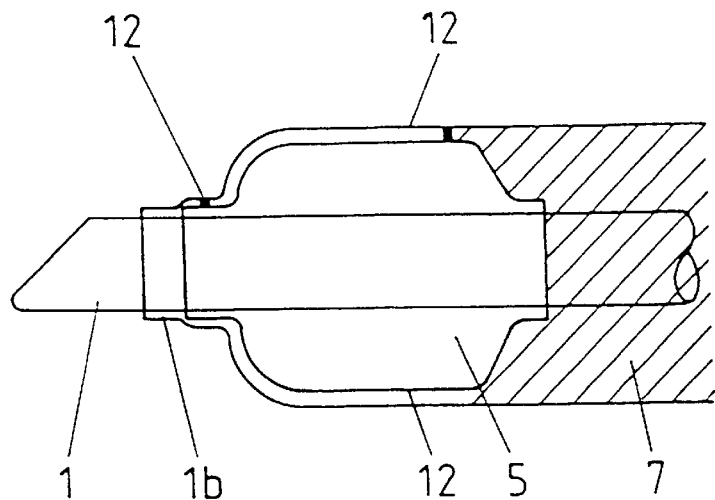
Figure 4:
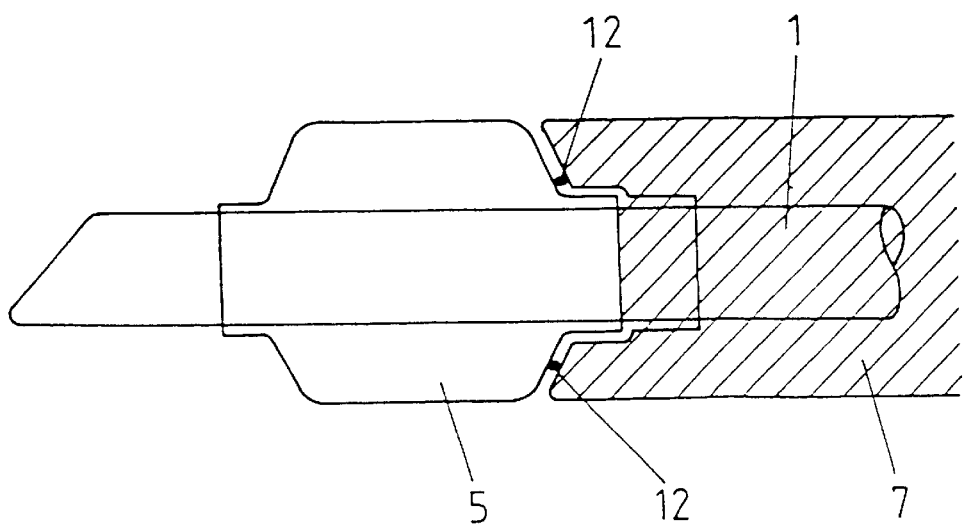
Figure 3A:
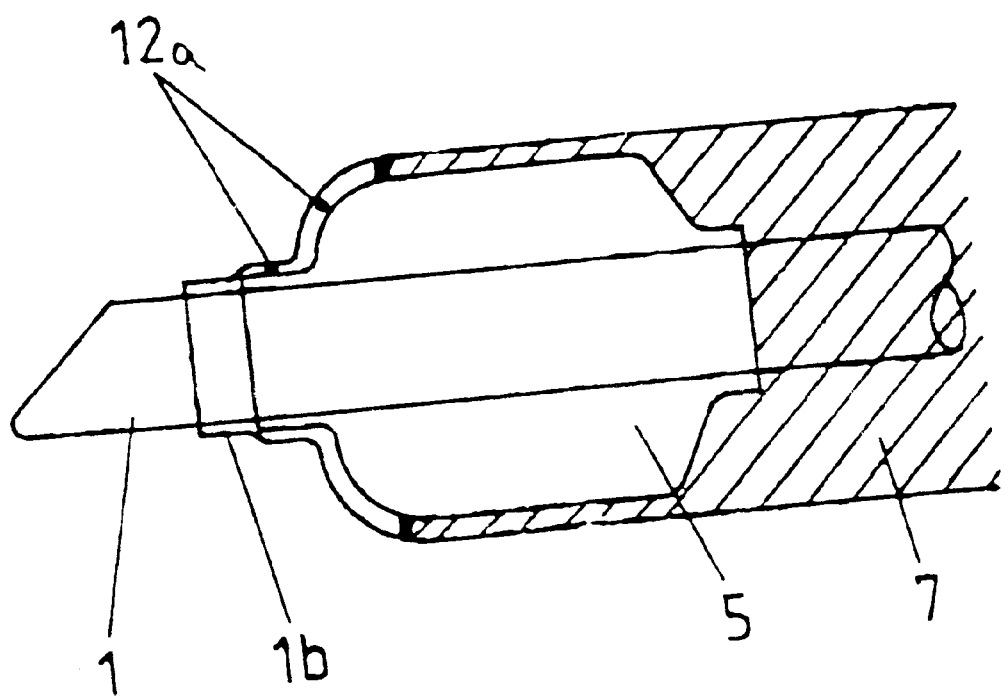
Figure 5:
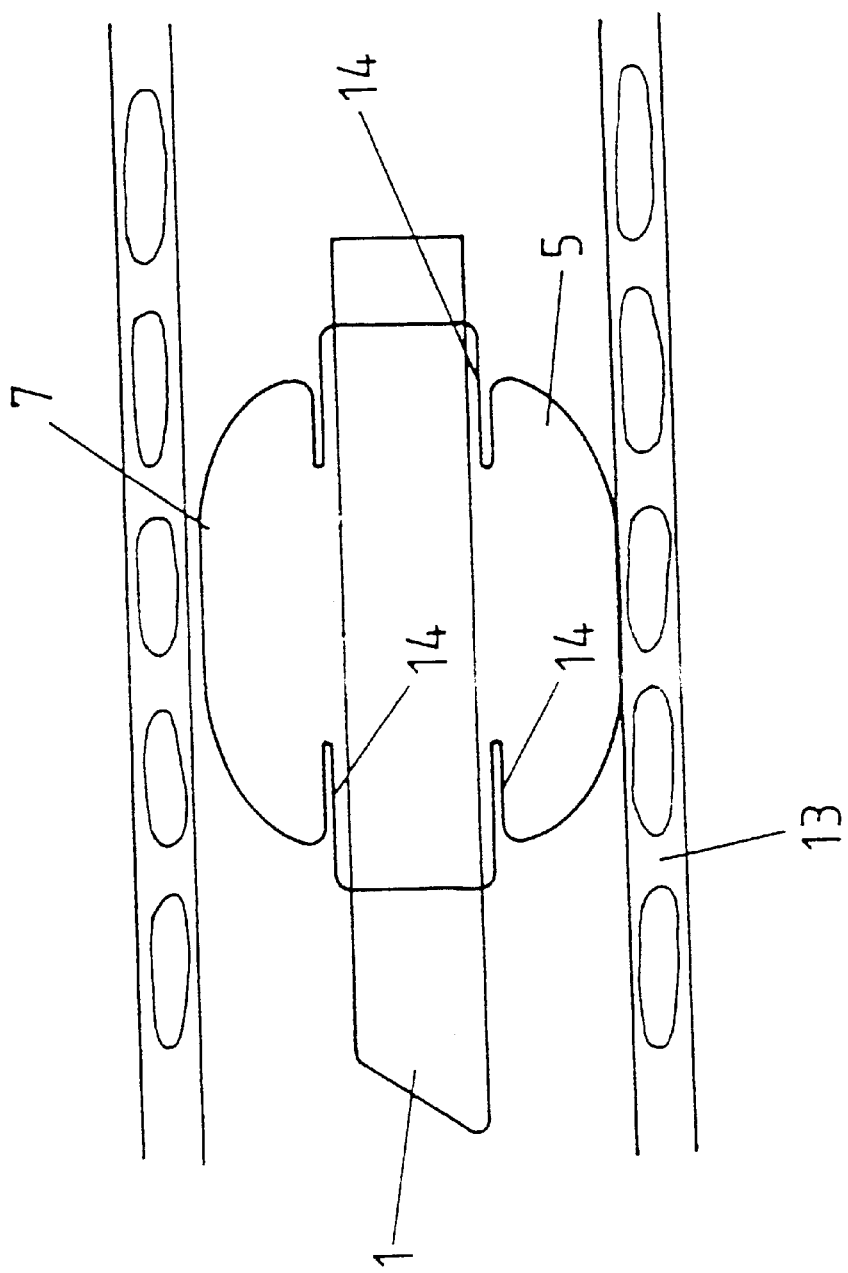

The invention is more fully explained by means of figures and examples of how it is employed. They show:

FIG. 1 A frontal section through the larynx, with the adjoining anatomical structures, as well as, shown within, a nasal or oral endotracheal tube with regulation cuff and the tampon-balloon attached above it;

FIG. 2 The structure of the device with tracheal tube, cuff, tampon-balloon and extracorporeal reservoir in a form recommended for operation of the invention;

FIG. 2a A pressure-equalizing balloon in unfilled state for a tracheal tube according to the invention;

FIG. 2b The pressure-equalizing balloon of FIG. 2a in filled, expanded condition;

FIG. 3 A detail of the invention;

FIG. 3a An enlarged example of the cuff and attached tampon-bladder according to a particular operational form;

FIG. 4 A variant of the detail of FIG. 3;

FIG. 5 A further detail of the invention.

In FIG. 1 are shown a tracheal tube 1 correctly placed endotracheally and its topographical relations with the relevant adjoining anatomical structures (larynx and upper respiratory passages). The tracheal tube 1 going from 1a cranially to 1b caudally passes the epiglottis 2, the region of the vocal cords 3 (glottis), and the subglottal space 4, adjacent to the vocal cords and bordered caudally by the upper margin of the cuff 5. Fixation of the tracheal tube 1 in the respiratory passages by a regular airtight cuff 5 results distal to the cricoid cartilage, at about at least the first upper tracheal ring 6. A clinical user often chooses also to blockade the tube in the middle third of the trachea to avoid accidental extubation of the patient.

At 7 is shown a tampon-balloon 7 (represented cross-hatched) filled with water (or another similar medium), which is attached cranially to the upper margin of the cuff and thereby fills the subglottal space 4. In the contact region of the tampon-bladder 7 with the cuff, the tampon-bladder is situated closely fitting to the cuff in a direction transverse to the respiratory cannula. The tampon-balloon optionally extends cranially up to in the region of the vocal cords 3 (glottis), up to in the supraglottal region 2 (vestibulum epiglotticum), or into the lower pharynx (hypopharynx).

In FIG. 2 the functional aspect of the invention is more precisely represented by a preferred operational form of the whole tracheal tube. Through a third channel 8 of the widest feasible bore, enclosed in the wall of a tracheal tube furnished with a conventional high volume/low pressure cuff 5, the tampon-balloon can be inflated with water (or some other similar medium, for instance gas) through a number of outlet apertures 9.

The tampon-balloon 7 is made of a foil-like, extremely elastic material which adapts closely without creases to the walls of the larynx. In order to ensure correct siting of the tracheal tube 1 and its tampon-balloon 7, the tampon-balloon is indicated locally by a coloured marker 10 corresponding to the later siting between the vocal cords 3.

Through channel 8 the water filling of the tampon-bladder is connected via a wide-bore connection to a scaled water-column 11 situated beside the patient. Following the principle of communicating pipes this reservoir ensures a continuous, shape-maintaining filling of tampon-balloon 7 without thereby placing the laryngeal structures themselves under stress.

In another embodiment shown in FIGS. 2, 2a and 2b, the open scaled water-column can be replaced by a flexible pressure-regulating balloon 11a which by the tension of its walls can maintain a solely shape-preserving pressure inside the subglottal tampon-bladder. For instance the balloon 11a is so designed that in an unfilled condition like that shown in example 11b it expands with correct filling to a geometrically symmetrical FIG. 11c and thus indicates optimal full pressure. Instead of the illustrated example 11b a preformed representation of the unfilled shape can be given (FIG. 2a) which on correct filling is restored to a geometrically symmetrical figure showing optimal full pressure (FIG. 2b).

The tampon-bladder and equalizing balloon can be filled with fluid or gaseous media.

The tampon-bladder is fixed to the tracheal tube 1 by e.g. adhesion, folding and welding, bandaging or similar means.

The material of the tampon-bladder 7 consists preferably of a soft body-compatible foil with properties resembling latex skin. It can affix itself to the anatomical structures of the subglottal space 4 with minimal stress to the walls and effectively without wrinkling. In addition it can in its shape be appropriately preformed to the subglottal space.

In accordance with a further embodiment, the tampon-bladder can be so configured that the diameter of the unfilled tampon-bladder is slightly greater than that of the subglottal space. Expansion of the tampon-bladder is superfluous inasmuch as tamponade of the subglottal space is epithelium-sparing and tolerated at still more marginal full pressures. The use of appropriately thinner wall materials creasing does not enhance the downflow of secretions.

Optionally, the material of the tampon-bladder can on creasing cling to itself spontaneously and so attach the crease tightly to itself. This easy adhesiveness is comparable for instance to the adhesiveness of artificial household foil.

As shown in FIG. 3, in an operational form of the invention the tampon-bladder 7 is completely pulled away over the cuff 5 and at the lower, caudal end of the tracheal tube 1b stuck to this and closed off. To prevent shifting of the balloon caudally, so-called herniation, the cuff 5 may be stuck to the tampon-bladder in the region of the common apposing surface 12.

Alternatively the cuff may be stuck only in the region of the common distal apposing surface 12a, thereby enabling a better separate inflation of cuff 5 and tampon-bladder. Correspondingly the fastening may be adhered to the common apposing surface 12a running across tracheal tube 1 only in the inflated state, as shown in FIG. 3a. The common apposing surface running parallel to tracheal tube 1 is not adhered.

In another embodiment of the invention, shown in FIG. 4, the fixation of the tampon-bladder 7 is connected cranially immediately to the upper margin of cuff 5. In the region of their common apposing surface cuff 5 and the tampon-bladder 7 are adhered at 12.

In order to minimize as far as possible shearing movements of cuff 5 against the tracheal wall 13, such as those similar for instance to the act of swallowing, the tracheal tube 1 is preferably placed movably in addition inside the cuff 5 (in all variants) within a certain circumference through a surrounding fold 14 in the region of the cuff attachment to the tracheal tube (see FIG. 5).

The principle of the sub- or supraglottal tamponade as carried out above can also be effected without an accompanying respiratory tube but solely through a free-standing hose connection with an extracorporeal reservoir. Protecting the larynx and trachea against downflowing secretions like this makes the invention usable also for patients with tracheotomies or ventilated through a tracheal cannula.

In the embodiments with the water-column the water pressure in tampon-bladders 7 and 16 is maintained usually only by the water-column until that of the water accumulated in reservoir 11 is reached, at which reservoir 11 stays at a level a little above the tampon-bladders 7 and 16. In this way a very constant, slightly above atmospheric, internal pressure is maintained for tampon-bladders 7 and 16.

What is claimed is:

1. A tracheal tube for placement in a middle or upper tracheal section of a patient, comprising:
   a high-volume, low-pressure fixing cuff having a shape to block a trachea beneath a glottis of the patient;
   a respiratory cannula disposed through said fixing cuff;
   a tampon-bladder disposed concentrically about said cuff, said tampon-bladder being made of flexible material and expansible by the influx of fluid, which when filled is different in shape from the shape of the cuff;
   said tampon-bladder being made from a material such that a shape-preserving pressure is distributed throughout the subglottic region when said tampon-bladder is in a full condition, said material being a sufficient length so as to occupy the subglottic space completely when said tampon-bladder is in the full condition exerting an epithelium-sparing pressure on subglottic structures.

2. Tracheal tube according to claim 1, wherein the tampon bladder is designed in such a way that it completely occupies the supraglottal as well as subglottal space.

3. Tracheal tube according to claim 1, wherein the tampon-bladder is preformed and adapted to the internal morphology of the larynx and glottis.

4. Tracheal tube according to claim 1, wherein the tampon-bladder encloses the cuff with its wall.

5. Tracheal tube according to claim 1, wherein the wall of the tampon-bladder is attached to the wall of the cuff, in at least part of the area of an common apposing surface of said wall of said cuff and said wall of the tampon-bladder.

6. Tracheal tube according to claim 5, wherein the tampon-bladder and the cuff are stuck to each other only on a common apposing surface running at right angles to the ventilating cannula in their filled condition.

7. The tracheal tube of claim 5, wherein the wall of the tampon-bladder is attached to the wall of the cuff by an adhesive.

8. Tracheal tube according to claim 1, wherein the respiratory cannula is movably disposed through said fixing cuff.

9. Tracheal tube according to claim 8, wherein the respiratory cannula is movably disposed through said fixing cuff through a surrounding fold in the region of a cuff attachment to the cannula.

10. Tracheal tube according to claim 1, wherein the fluid is a liquid and wherein the tracheal tube further comprises a plurality of liquid columns wherein an adjustment of pressure in the tampon-bladder is made only by one of the plurality of liquid columns equipped with fluid under atmospheric pressure.

11. The tracheal tube of claim 10, wherein the fluid is water.

12. Tracheal tube according to claim 1, wherein an inner cavity of the tampon-bladder is connected via a channel with an equalizing receptacle.

13. Tracheal tube according to claim 1, wherein a pressure source for the cuff can be operated independently of a fluid pressure source of the tampon-bladder.

14. Tracheal tube according to claim 1, wherein a channel supplying the tampon-bladder with fluid is equipped with a number of outflow orifices in the region of the tampon bladder communicating with the channel via the internal cavity of the tampon-bladder.

15. Tracheal tube according to claim 1, wherein the tampon-bladder is made of a material resembling latex skin, easily self-adherent when folded.

16. Tracheal tube according to claim 1, wherein the tampon-bladder is preformed and in unfilled condition as a larger diameter than the diameter of the subglottal space.

17. A tracheal tube for placement in a middle or upper tracheal section of a patient, comprising:
    a fixing cuff having a shape, said fixing cuff being sized to block a trachea, or an identified diameter, beneath a glottis of the patient and fix the tracheal tube within the trachea; and
    a tampon-bladder disposed concentrically about said fixing cuff with an inner side of said tampon-bladder facing said fixing cuff,
    said tampon-bladder being made of a flexible material and expansible by an influx of fluid, the tampon bladder when filled having a different shape different from the shape of said cuff,
    said material being such that a shape-preserving preserving pressure is distributed throughout the subglottic region when said tampon-bladder is in a full condition,
    said material being a sufficient length so as to occupy the subglottic space completely when said tampon-bladder is in the full condition exerting a epithelium-sparing pressure on subglottic structures.

18. The tracheal tube of claim 17, wherein said fixing cuff is a high-volume, low-pressure fixing cuff,
    the high-volume, low-pressure fixing cuff having, in a freely unfolded and non stretched state, a diameter exceeding the identified diameter of the trachea.

19. A tracheal tube for placement in a middle or upper tracheal section of a patient, comprising:
    a fixing cuff sized to block a trachea beneath a glottis of the patient and fix the tracheal tube within the trachea,
    the fixing cuff, in an inflated state, having a diameter exceeding an identified diameter of the trachea; and
    a tampon-bladder disposed concentrically about said fixing cuff,
    said tampon-bladder being made of a flexible material and expansible by an influx of fluid,
    said tampon-bladder being sized to completely occupy the subglottic space when filled within an epithelium-sparing pressure,
    said tampon-bladder being sized to occupy the subglottic space completely when in a full condition exerting the epithelium-sparing pressure on subglottic structures,
    wherein the tracheal tube is identified as being sized for the identified diameter of the trachea.

20. The trachea tube of claim 19, wherein said tampon-bladder has a diameter in an unfilled state greater than an identified diameter of the subglottal space.

21. The tracheal tube of claim 19, wherein said fixing cuff is a high-volume, low-pressure fixing cuff.

* * * * *